(12) United States Patent
Yildirim

(10) Patent No.: US 11,389,664 B2
(45) Date of Patent: Jul. 19, 2022

(54) LIGHT THERAPY DEVICES AND SYSTEMS

(71) Applicant: L'OREAL, Paris (FR)

(72) Inventor: Ozgur Emek Yildirim, Bellevue, WA (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 16/711,986

(22) Filed: Dec. 12, 2019

(65) Prior Publication Data
US 2021/0178180 A1    Jun. 17, 2021

(51) Int. Cl.
*A61N 5/06*    (2006.01)

(52) U.S. Cl.
CPC .... *A61N 5/0616* (2013.01); *A61N 2005/0645* (2013.01); *A61N 2005/0651* (2013.01); *A61N 2005/0662* (2013.01); *A61N 2005/0666* (2013.01)

(58) Field of Classification Search
CPC .......... A61N 5/0616; A61N 2005/0666; A61N 2005/0651; A61N 2005/0662; A61N 2005/0645
See application file for complete search history.

(56) References Cited

U.S. PATENT DOCUMENTS

| | | | |
|---|---|---|---|
| 9,355,345 B2 * | 5/2016 | Powell | G06K 19/0614 |
| 9,744,378 B2 | 8/2017 | Tapper et al. | |
| 2013/0190845 A1 * | 7/2013 | Liu | A61N 5/0616 607/90 |
| 2018/0140867 A1 * | 5/2018 | Levatter | A61N 5/062 |

OTHER PUBLICATIONS

"Decent Lighting Solutions," MEMSLUX. (6 pages).

* cited by examiner

*Primary Examiner* — Carl H Layno
*Assistant Examiner* — Aya Ziad Bakkar
(74) *Attorney, Agent, or Firm* — Christensen O'Connor Johnson Kindness PLLC

(57) ABSTRACT

Light therapy devices and systems configured to apply light to a portion of skin are described. In an embodiment, the light therapy device comprises a sheet defining two opposing major sides, wherein the sheet is configured to transmit light through the sheet by internal reflection, and wherein a portion of a light emission side of the two opposing major sides is configured to couple with the portion of skin and defines micropatterning configured to emit light from within the sheet; and a light source configured to emit light into the sheet between the two opposing major sides.

7 Claims, 4 Drawing Sheets

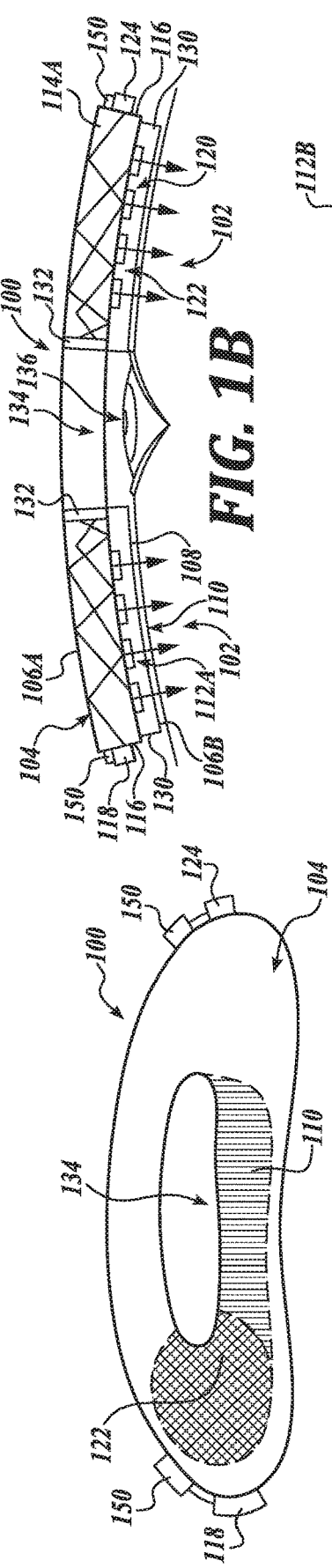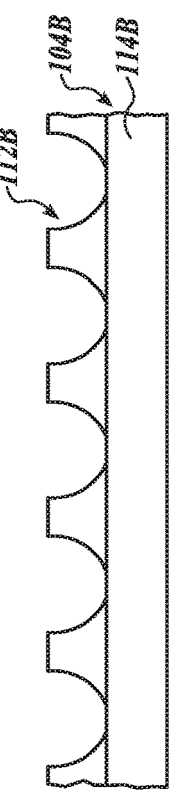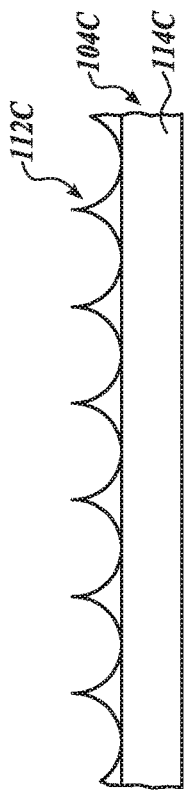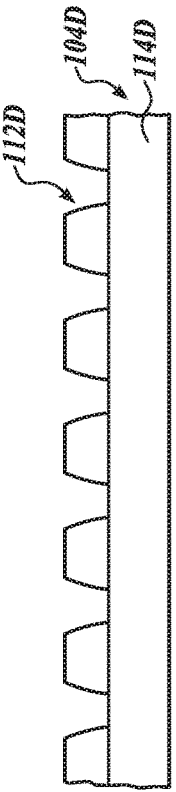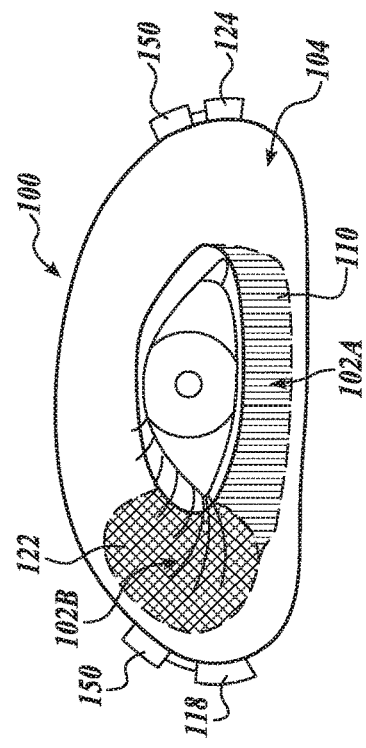
FIG. 1A
FIG. 1B
FIG. 1C
FIG. 1D
FIG. 1E
FIG. 1F

LIGHT THERAPY DEVICES AND SYSTEMS

SUMMARY

In one aspect, the present disclosure provides a light therapy device configured to apply light to a portion of skin. In an embodiment, the light therapy device generally includes a sheet defining two opposing major sides, wherein the sheet is configured to transmit light through the sheet by internal reflection, and wherein a portion of a light emission side of the two opposing major sides is configured to couple with the portion of skin and defines micropatterning configured to emit light from within the sheet; and a light source configured to emit light into the sheet between the two opposing major sides.

In another aspect, the present disclosure provides a system for light therapy configured to apply light to a portion of skin. In an embodiment, the system generally includes a sheet defining two opposing major sides, wherein the sheet is configured to transmit light through the sheet by internal reflection, and wherein a portion of a light emission side of the two opposing major sides is configured to couple with the portion of skin and defines micropatterning configured to emit light from within the sheet; a light source configured to emit light into the sheet between the two opposing major sides; and a controller operatively coupled to the light source, the controller including logic that, when executed by the controller, causes the system to perform operations including: emitting light with the light source into the sheet.

In accordance with any of the embodiments disclosed herein, the micropatterning is positioned distal from the light source.

In accordance with any of the embodiments disclosed herein, the micropatterning is configured to emit light of a first wavelength range at a first intensity. In accordance with any of the embodiments disclosed herein, the micropatterning is configured to emit light of a second wavelength range different than the first wavelength range at a second intensity different than the first intensity.

In accordance with any of the embodiments disclosed herein, the light therapy device defines second micropatterning disposed on a second portion of the light emission side. In accordance with any of the embodiments disclosed herein, the second micropatterning is configured to emit light of a second wavelength range different than the first wavelength range at a second intensity different than the first intensity.

In accordance with any of the embodiments disclosed herein, the light source is a first light source configured to emit first light having a first wavelength range, the light therapy device further comprising a second light source configured to emit second light. In accordance with any of the embodiments disclosed herein, the second light source is positioned to emit the second light into the sheet between the two opposing major sides. In accordance with any of the embodiments disclosed herein, the second light has a second wavelength range different than the first wavelength range.

In accordance with any of the embodiments disclosed herein, the light therapy device or system includes a second sheet defining two second opposing major sides, wherein the second sheet is configured to transmit light by internal reflection, wherein a portion of a second light emission side of the two second opposing major sides defines second micropatterning configured to emit light, and wherein the second light source is configured to emit the second light into the second sheet between the second two opposing major sides.

In accordance with any of the embodiments disclosed herein, the light therapy device or system includes a filter configured to filter light of a wavelength range emitted from the micropatterning.

In accordance with any of the embodiments disclosed herein, the light therapy device or system includes a mirror positioned to reflect light within the sheet.

In accordance with any of the embodiments disclosed herein, the light emission side of the sheet is configured to face the portion of skin when the sheet is coupled to the portion of skin, and wherein the sheet is configured to conform to the portion of skin.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of the claimed subject matter will become more readily appreciated as the same become better understood by reference to the following detailed description, when taken in conjunction with the accompanying drawings, wherein:

FIG. 1A is a top-down plan view of a light therapy device, in accordance with an embodiment of the disclosure;

FIG. 1B is a cross-section view of the light therapy device of FIG. 1A, in accordance with an embodiment of the disclosure;

FIG. 1C is another top-down plan view of the light therapy device of FIG. 1A shown placed over a portion of skin, in accordance with an embodiment of the disclosure;

FIG. 1D is a cross-section view of a sheet defining micropatterning, in accordance with an embodiment of the disclosure;

FIG. 1E is a cross-section view of a sheet defining micropatterning, in accordance with an embodiment of the disclosure;

FIG. 1F is a cross-section view of a sheet defining micropatterning, in accordance with an embodiment of the disclosure;

Figure 2A:
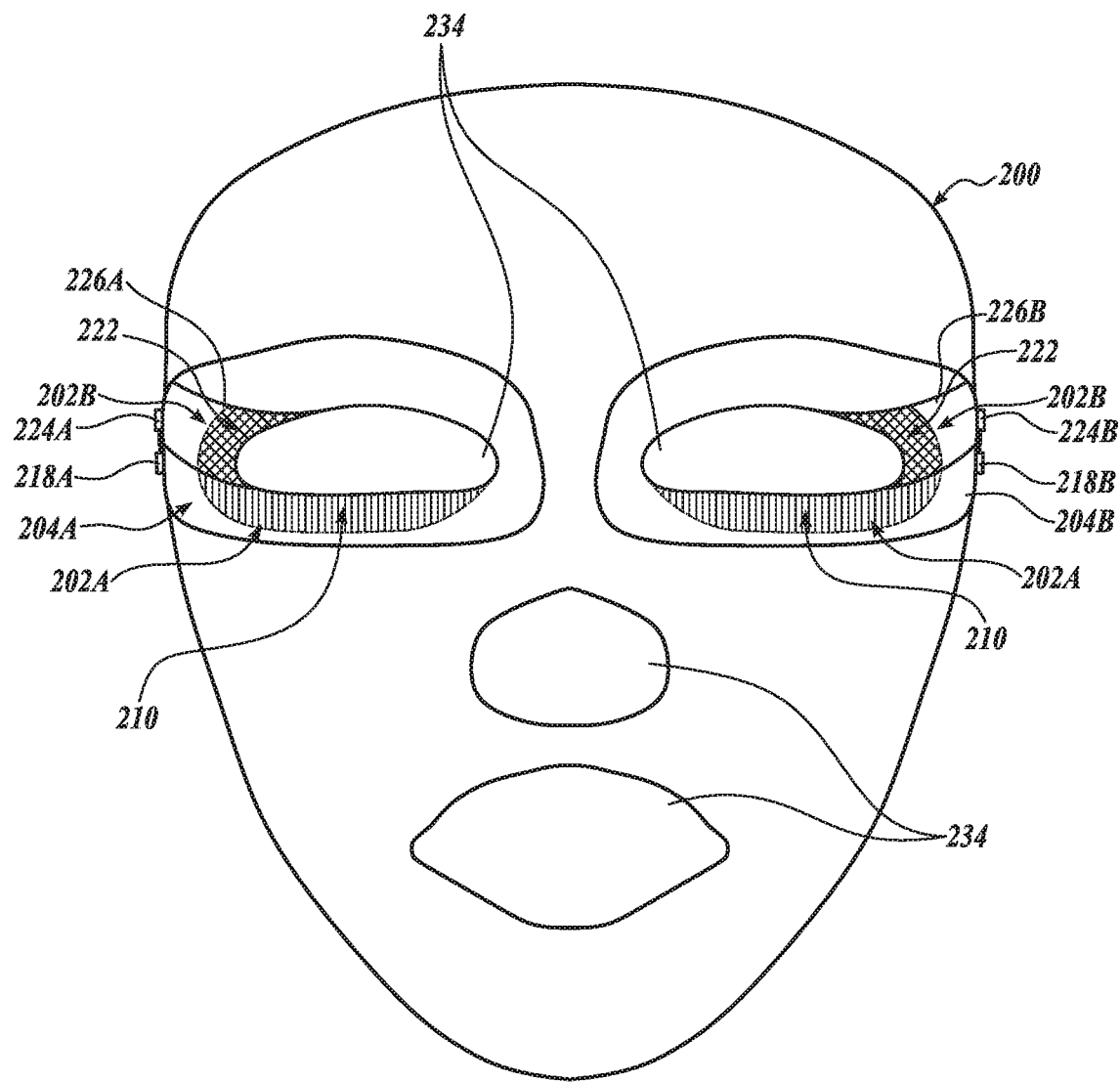
FIG. 2A is a top-down plan view of a light therapy device, in accordance with an embodiment of the disclosure.

Aspects and many of the attendant advantages of the claimed subject matter will become more readily appreciated as the same become better understood by reference to the following detailed description, when taken in conjunction with the accompanying drawings.

The detailed description set forth below in connection with the appended drawings, where like numerals reference like elements, is intended as a description of various embodiments of the disclosed subject matter and is not intended to represent the only embodiments. Each embodiment described in this disclosure is provided merely as an example or illustration and should not be construed as preferred or advantageous over other embodiments. The illustrative examples provided herein are not intended to be exhaustive or to limit the claimed subject matter to the precise forms disclosed.

DETAILED DESCRIPTION

Described herein are devices and systems for light therapy for application of light onto a portion of skin. Application of light to skin can have many advantageous and therapeutic effects on the skin.

Certain conventional light therapy devices include light sources located at or immediately adjacent to a position on the light therapy device from which the light is emitted. In this regard, a position of the light sources in such conventional light therapy devices is tied to the position in the device from which light is emitted, such as on a mask or patch applied to the portion of skin. Such a conventional design places constraints and requirements on, for example, the weight, size, and/or type of light source that can be used in light therapy devices.

It would be advantageous to avoid such constraints and requirements by placing light sources of a light therapy device distal from a portion of the light therapy device from which light is emitted onto a portion of skin.

Toward that end, the present disclosure provides light therapy devices and systems including a sheet defining micropatterning configured to emit light from within the sheet, and a light source configured to emit light into the sheet, such as between two opposing major sides of the sheet. As discussed further herein, such light therapy devices and systems enable a much broader design space by relaxing the constraint to position light sources carefully relative to the treatment areas. In the light therapy devices and system of the present disclosure, the light emitted by the light source is transported and emitted to the treatment areas, such as those including micropatterning, through the sheet by internal reflection. The light is emitted from the regions including the micropatterning, such as at a desired intensity. In this regard, the light emission intensity can be defined by design and placement of the micropatterning. Additionally or alternatively, active control features can be incorporated into the design to allow a level of dynamic control of the light intensity by location on the sheet, as described in further detail below. The sheet can be made to be flexible and conformable to the topography of the treatment area, helping increase its efficiency. Moreover, the light source or light sources can be configured to pump light having multiple nominal wavelength ranges into the sheet, wherein such different wavelengths of light diffract differently on the micropatterning and are, therefore, emitted from the sheet differently to fine tune the locations, intensities, and wavelength ranges emitted from the sheet In the following description, numerous specific details are set forth in order to provide a thorough understanding of one or more embodiments of the present disclosure. It will be apparent to one skilled in the art, however, that many embodiments of the present disclosure may be practiced without some or all of the specific details. In some instances, well-known process steps have not been described in detail in order not to unnecessarily obscure various aspects of the present disclosure. Further, it will be appreciated that embodiments of the present disclosure may employ any combination of features described herein.

A light therapy device 100, in accordance with an embodiment of the disclosure, will now be described with reference to FIGS. 1A-1F. FIG. 1A is a top-down plan view of a light therapy device 100. FIG. 1B is a cross-section view of the light therapy device 100. FIG. 1C is another top-down plan view of the light therapy device 100 shown placed over a portion of skin 102, in accordance with an embodiment of the disclosure.

In the illustrated embodiment, the light therapy device 100 is shown to include a sheet 104, a light source 118, and a power source 150 operatively coupled to the light source 118 to provide power thereto. As shown in FIG. 1B, the sheet 104 defines two opposing major sides 106A and 106B. Further, the light source 118 is positioned to emit light into the sheet 104 between the two opposing major sides 106A and 106B, such as at an edge 116 of the sheet 104 orthogonal to the two opposing major sides 106A and 106B. Such light emitted from the light source 118 is transmitted through the sheet 104 by internal reflection. In that regard, the light is shown reflecting off of the two opposing major sides 106A and 106B as it travels between the two opposing major sides 106A and 106B through the sheet 104.

The sheet 104 is generally planar defining the two opposing major sides 106A and 106B. In an embodiment, the sheet 104, while being generally planar and two-dimensional, is also flexible and configured to conform to a portion of skin.

In an embodiment, the sheet 104 includes a flexible glass substrate 114A. In an embodiment, the micropatterning 112A is etched into the flexible glass substrate 114A or into a photoresist disposed on the flexible glass substrate 114A. In an embodiment, the micropatterning 112A defines a number of three-dimensional structures having, for example, heights and widths on a scale in a range of about 1 micrometer to about 1,000 micrometers. In an embodiment, the light therapy device 100 includes a metal layer disposed between the flexible glass substrate 114A and the photoresist, the metal layer defining a number of a perforations or apertures corresponding to apertures defined by the micropatterning 112A.

As above, the sheet 104 includes micropatterning 112A configured to emit light from within the sheet 104. As shown in FIG. 1B, the micropatterning 112A, illustrated here as a plurality of crenellations projecting from a light emission side 108 of the two opposing major sides 106A and 106B, emits light from within the sheet 104. Such emission is in contrast to the other of the two opposing major sides 106A and 106B, which reflects the light by total internal reflection. In an embodiment, light transmitted in the sheet 104 is transmitted by total internal reflection off of the two opposing major sides 106A and 106B except in portions of the two opposing major sides 106A and 106B that define the micropatterning 112A.

In the illustrated embodiment, the light emission side 108 of the sheet 104 is configured to face the portion of skin 102A when the sheet 104 is coupled to the portion of skin 102A. In order to direct the light emitted from the light emission side 108 to the portion of skin 102A, the sheet 104 may be flexible or otherwise suitable to conform to the portion of skin 102A, thereby increasing an amount of light emitted from the micropatterning 112A that reaches the portion of skin 102A coupled thereto.

While micropatterning 112A defined by a plurality of crenellations projecting from a light emission side 108 of the sheet 104 are illustrated in FIG. 1B, it will be understood that micropatterning 112A having other shapes also configured to emit light from within the sheet 104 are within the scope of the present disclosure. In that regard, attention is directed to FIGS. 1D-1F in which sheets 104B-104D defining micropatterning 112B-112D, in accordance with embodiments of the disclosure, are illustrated.

FIG. 1D is a cross-section view of a sheet 104B defining micropatterning 112B, in accordance with an embodiment of the disclosure. As shown, the micropatterning 112B defines a number of projections from a substrate 114B defining mesas at a high point and returning to one of the two opposing major sides of the substrate 114B in a concave arcuate shape.

FIG. 1E is a cross-section view of a sheet 104C defining micropatterning 112C, in accordance with an embodiment of the disclosure. As shown, the micropatterning 112C defines a number of projections from a substrate 114C having sharp points that gradually return to one of the two opposing major surfaces of the substrate 114C in a concave arcuate shape.

FIG. 1F is a cross-section view of a sheet 104D defining micropatterning 112D, in accordance with an embodiment of the disclosure. As shown, the micropatterning 112D defines a number of projections from one of the two opposing major surfaces of a substrate 114D having a funnel-like shape in which each projection defines a mesa at a high point and returns to one of the two opposing major sides of the substrate 114D in a convex arcuate shape.

In the illustrated embodiment of FIGS. 1B and 1C, the light emission side 108 of the sheet 104 is shown coupled to a portion of skin 102A. In that regard, light emitted from the light emission side 108 through the micropatterning 112A impinges upon the portion of skin 102A. In an embodiment, the other of the two opposing major sides 106A and 106B does not include micropatterning 112A. In this regard, in an embodiment, the other of the two opposing major sides 106A and 106B does not emit or does not substantially emit light from within the sheet 104.

In an embodiment the micropatterning 112A covers a portion 110 of the light emission side 108. In an embodiment, the micropatterning 112A does not cover an entirety of the light emission side 108. In the illustrated embodiment, the micropatterning 112A is disposed distal from the light source 118. As shown in FIG. 1C, the portion 110 of the light emission side 108 defining the micropatterning 112A is positioned to be adjacent to a portion of skin 102A underneath an eye 136 when the sheet 104 is coupled to the portion of skin 102A. The light source 118, by contrast is positioned in a portion of the light therapy device 100 closer to a corner of the eye 136 when the light therapy device 100 is coupled to the portion of skin 102A. In this regard, light emitted from the light source 118 into the sheet 104 is reflected internally until it reaches the micropatterning 112A where some or all of the light is emitted from the micropatterning 112A. Such a configuration allows the light source 118 to be positioned away from an emission position on the sheet 104. This allows the light source 118 to be relatively free of constraints, such as in size, weight, power demands, etc., that would be placed on a light source 118 positioned at or immediately adjacent to an emission position.

Furthermore, because only a portion 110 of the light emission side 108 defines micropatterning 112A configured to emit light from within the sheet 104, light is not or is not substantially emitted from other portions of the light emission side 108, which do not define such micropatterning 112A. In this regard, the light emission side 108 is configured to emit light from within the sheet 104 in only select portions, such as those including micropatterning 112A, thereby targeting by design certain portions of skin for light therapy treatment.

In an embodiment, the micropatterning 112A is configured to emit light of a first wavelength range at a first intensity. In an embodiment, the micropatterning 112A is configured to emit light of a second wavelength range different than the first wavelength range at a second intensity different than the first intensity. In this regard, the micropatterning 112A is configured to emit light of different wavelength ranges at different intensities. Such differential emission characteristics may be defined or tuned, for example, by a shape or size of the micropatterning 112A itself, with one micropatterning 112A shape or size preferentially emitting light of a first light wavelength range over a second wavelength range.

Emitting light having an intensity tuned with respect to wavelength ranges is suitable to provide light therapy to the portion of skin 102A according to a preferred or predetermined wavelength range. Light having different wavelength ranges is suitable to initiate different effects in portions of skin. For example, light having wavelengths in a range of about 625 nm to about 700 nm is suitable to provide anti-aging effects, light having wavelengths in a range of about 400 nm to about 420 nm is suitable to illicit cell rejuvenation, light having wavelengths in a range of about 440 nm to about 500 nm is suitable to provide anti-acne benefits, light having wavelengths in a range of about 500 nm to about 520 nm is suitable to provide skin soothing effects, and light having wavelengths in a range of about 520 nm to about 565 nm is suitable to provide skin balancing effects, light having wavelengths in a range of about 565 nm to about 590 nm is suitable to reduce redness in a portion of skin 102A, and light having wavelengths in a range of about 590 nm to about 625 nm is suitable to revitalize a portion of skin 102A.

Accordingly, in an embodiment, the micropatterning 112A is configured to allow light having one or more of the above wavelength ranges to pass through the micropatterning 112A from within the sheet 104. Correspondingly, in an embodiment, the light source 118 is configured to emit light having wavelengths in one or more of the above wavelength ranges. In an embodiment, the light source 118 is configured to emit light in an ultraviolet wavelength range (e.g. from about 10 nm to about 400 nm), a visible light range (e.g. from about 400 nm to about 700 nm), an infrared wavelength range (e.g. from about 700 nm to about 1 mm), and combinations thereof.

The light source 118 can include any light source 118 configured shaped to emit light into the sheet 104 described herein. In an embodiment, the light source 118 is selected from a light-emitting diode, an incandescent bulb, a halogen lamp, a laser, and the like.

The light therapy device 100 is shown to include a second light source 124. In an embodiment, the light source 118 is a first light source 118. In an embodiment, the light source 118 is a first light source 118 configured to emit first light having a first wavelength range, wherein the second light source 124 is configured to emit second light, such as between the two opposing major sides 106A and 106B and into the sheet 104. In an embodiment, the first wavelength range and the second wavelength range are partially or entirely overlapping. In an embodiment, the second light has a second wavelength range different than the first wavelength range. In this regard, in an embodiment, the first and second light sources 118 and 124 are configured to emit light having different wavelength ranges. In an embodiment, such first and second light are suitable to provide different effects to a portion of skin 102A exposed thereto, as described further hereinabove.

In the illustrated embodiment, the sheet 104 is shown to define second micropatterning 120 on a second portion 122 of the light emission side 108 of the sheet 104. Such a second portion of micropatterning 120 is suitable to provide light therapy to a second portion of skin 102B as light is emitted from the second portion of micropatterning 120. In an embodiment, the second micropatterning 120 is configured to emit light of a second wavelength range different than light emitted from the first micropatterning 112A in a first wavelength range. In an embodiment, the second micropatterning 120 is configured to emit the light of a second wavelength range at a second intensity different than an intensity of the first light emitted from the first micropatterning 112A. For example, the first micropatterning 112A may be configured to emit first light from the first light source 118, whereas the second micropatterning 120 may be configured to emit the second light from the second light source 124. Likewise, in an embodiment, the first micropatterning 112A is configured to emit light from both the first and second light sources 118 and 124 at different intensities than the second micropatterning 120.

In this regard, the light therapy device 100 may be configured to emit light having different wavelength ranges, such as from different light sources, onto different portions of skin coupled thereto. Referring to FIGS. 1A and 1C, the first portion 110 of the light emission side 108, positioned to emit light over a portion of skin 102A beneath an eye 136, may be configured, in an embodiment, to emit light having wavelengths in a range of about 400 nm to about 420 nm, suitable to illicit cell rejuvenation, such as to reduce bags or dark circles under the eye 136. Likewise, in an embodiment, the second portion 122 of the light emission side 108, positioned to emit light over a portion of skin 102B adjacent to a corner of the eye 136, is configured to emit light having wavelengths in a range of about 625 nm to about 700 nm, suitable to provide anti-aging effects, such as to reduce wrinkles.

The light therapy device 100 is shown to define an aperture 134. In the illustrated embodiment, the aperture 134 is shaped to be positioned over an eye 136 such that a user can see through the aperture 134 while the sheet 104 is applied to a portion of skin 102A adjacent to the eye 136. While a sheet 104 defining an aperture 134 is shown, it will be understood that sheets not defining an aperture 134, such as in the form of a patch, are within the scope of the present disclosure.

In the illustrated embodiment of FIG. 1B, the light therapy device 100 is also shown to include mirrors 132 disposed within sheet 104 adjacent to the aperture 134. The mirrors 132 are positioned to reflect light emitted by the light source 118 as it is transmitted through the sheet 104 suitable to further propagate internal reflection of light.

The light therapy device 100 is shown to further include a filter 130 positioned over the micropatterning 112A and 120. In this regard, the filter 130 is positioned to filter light emitted from the micropatterning 112A and 120 and, thus, filter light of a wavelength range emitted from the micropatterning 112A and 120 before impinging upon the portions of skin 102A and 102B. Such a filter 130 is suitable to filter out light emitted by the first light source 118 and/or second light source 124 having a particular wavelength range not already filtered by the micropatterning 112A and 120.

Figure 2B:
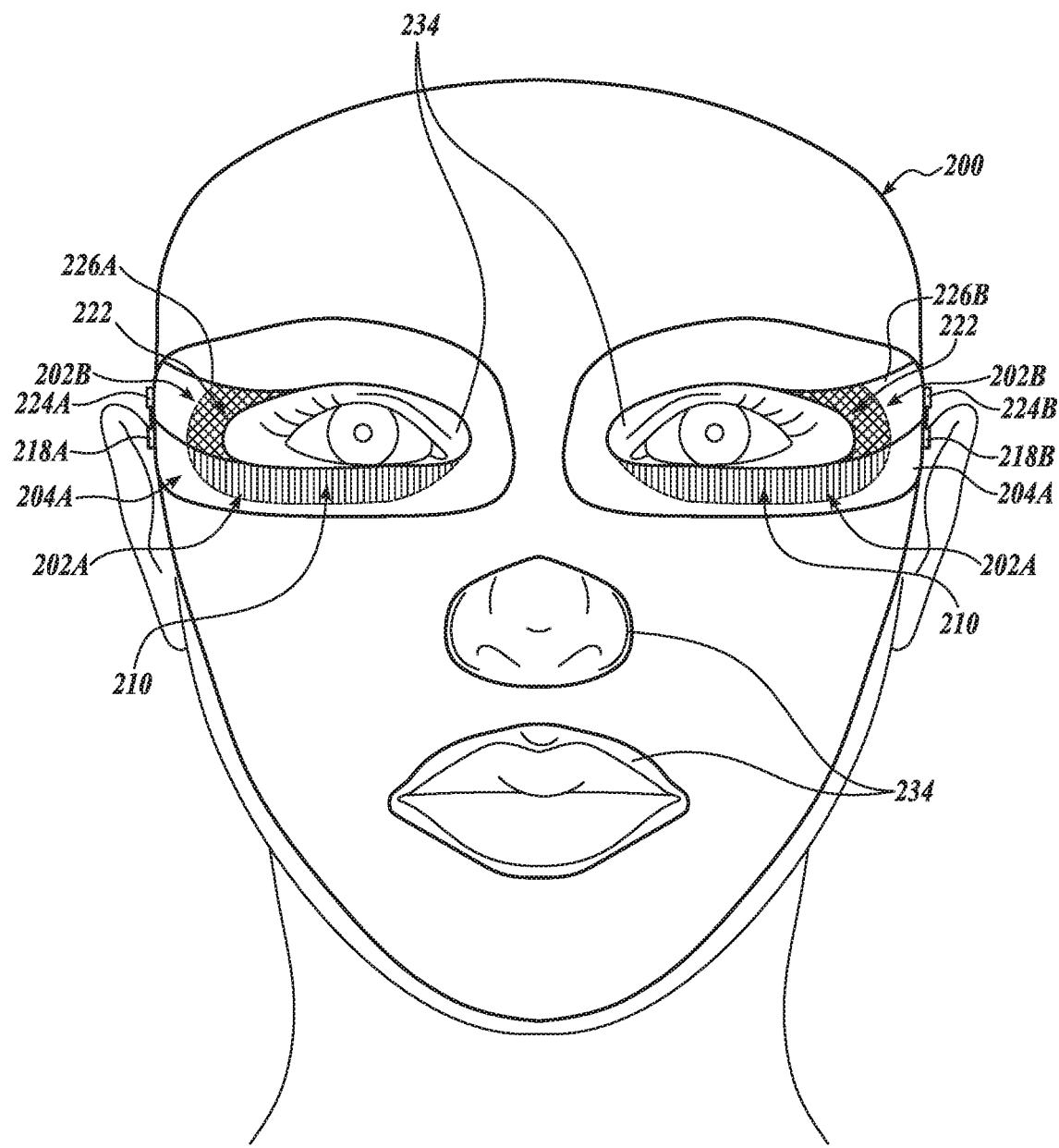
FIG. 2B is another top-down plan view of the light therapy device of FIG. 2A shown placed over a portion of skin, in accordance with an embodiment of the disclosure.

In an embodiment, the light therapy devices of the present disclosure comprise two or more sheets configured to transmit light by internal reflection and defining micropatterning configured to emit light from within the sheet. In that regard, attention is directed to FIGS. 2A and 2B in which a light therapy device 200, in accordance with an embodiment of the disclosure, is illustrated. FIG. 2A is a top-down plan view of the light therapy device 200, in accordance with an embodiment of the disclosure. FIG. 2B is another top-down plan view of the light therapy device 200 shown placed over a portion of skin 202A.

As shown, the light therapy device 200 includes a first sheets 204A and 204B shaped and positioned to couple with a first portion of skin 202A, including a portion of skin 202A disposed under an eye, when the light therapy device 200 is coupled to a face of a user. A portion 210 of the first sheets 204A and 204B also define first micropatterning positioned to emit light from within the first sheets 204A and 204B onto the portion of skin 202A disposed under the eye. In the illustrated embodiment, the light therapy device 200 is shown to include first light sources 218A and 218B configured to emit light including light having wavelengths suitable to provide light therapy to the portion of skin 202A adjacent to the first micropatterning. In this regard, in an embodiment, the first light sources 218A and 218B are configured to emit light having wavelengths in a range of about 400 nm to about 420 nm is suitable to illicit cell rejuvenation, such as to reduce bags or dark circles under the eye. Likewise, in an embodiment, the first micropatterning is configured to emit light from within the sheet having a wavelength range overlapping with the first light emitted from the first light sources 218A and 218B.

The light therapy device 200 is also shown to include second light sources 224A and 224B configured to emit second light. As shown, the second light sources 224A and 224B are optically coupled to second sheets 226A and 226B. In an embodiment, such second sheets 226A and 226B defines two second opposing major sides, wherein the second sheets 226A and 226B are configured to transmit light by internal reflection, as discussed further herein with respect to, for example, FIG. 1B. In such an embodiment, the second light sources 224A and 224B are configured to emit the second light into the second sheets 226A and 226B between the second two opposing major sides such that the second light is internally reflected within the second sheets 226A and 226B.

In an embodiment, the second sheets 226A and 226B include a portion 222 of a second light emission side of the two second opposing major sides defining second micropatterning configured to emit light. In an embodiment, such second micropatterning is configured to emit the second light emitted from the second light sources 224A and 224B. In this regard, the light therapy device 200 is configured to emit the second light, or a portion thereof, onto a portion of skin 202B coupled to the second light emission side of the second sheets 226A and 226B. In the illustrated embodiment, the second sheets 226A and 226B define second micropatterning positioned to emit light onto a portion of skin 202B including a corner of an eye, such as including wrinkles. In an embodiment, the second light sources 224A and 224B and second micropatterning are configured to emit second light including wavelengths in a range of wavelengths in a range of about 625 nm to about 700 nm suitable to provide anti-aging effects, such as to reduce wrinkles.

In an embodiment, the first and second sheets 204A, 204B, 226A, and 226B are optically isolated from one another. In this regard, in an embodiment, first light emitted from the first light sources 218A and 218B into the first sheets 204A and 204B is transmitted by the first sheets 204A and 204B by internal reflection, but the first light is not transmitted by or into the second sheets 226A and 226B. Likewise, in an embodiment, second light emitted by the second light sources 224A and 224B is transmitted by the second sheets 226A and 226B by internal reflection but is not transmitted by or into the first sheets 204A and 204B. In this regard, the light therapy device 200 is configured to target first light for emission from the first micropatterning and the second light for emission by the second micropatterning and corresponding portions of skins optically coupled thereto. Such targeted emission provides the capability to direct light of predetermined wavelengths to predetermined portions of skin coupleable to the light emission side of the light therapy device 200.

As above, the light therapy device 200 is shaped to couple to a portion of skin of a user. In the illustrated embodiment, the light therapy device 200 has the form of a mask shaped to coupled to a face of a user. As shown, the light therapy device 200, including the first sheets 204A and 204B and second sheets 226A and 226B, define a number of apertures 234 shaped to provide the eyes, nose, and mouth of the user easy access through the light therapy device 200.

Figure 3:
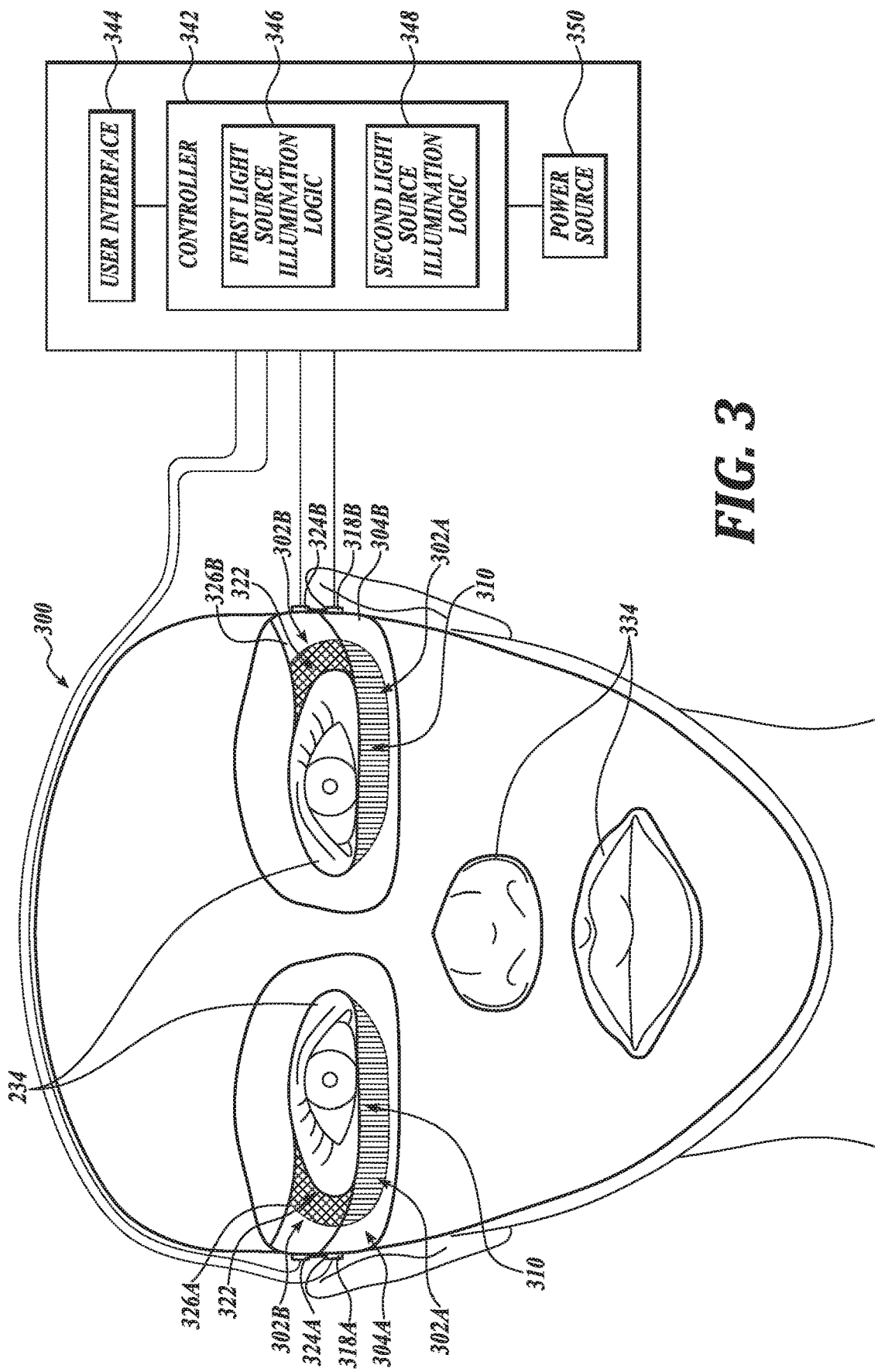
FIG. 3 is top-down plan view of a light therapy system, in accordance with an embodiment of the disclosure.

In another aspect, the present disclosure provides systems for light therapy. In that regard, attention is directed to FIG. 3 in which a light therapy system 301, in accordance with an embodiment of the disclosure is illustrated. FIG. 3 is top-down plan view of the light therapy system 301, in accordance with an embodiment of the disclosure.

In the illustrated embodiment, the system 301 is shown to include first and second sheets 304A, 304B, 326A, and 326B each including portions 310 and 322, respectively, configured to transmit light by internal reflection and defining micropatterning configured to emit light from within the sheets 304A, 304B, 326A, and 326B and light sources 318A, 318B, 324A, and 324B operatively coupled to the first and second sheets 304A, 304B, 326A, and 326B configured to emit light into the first and second sheets 304A, 304B, 326A, and 326B, respectively. In an embodiment, each of the first and second sheets 304A, 304B, 326A, and 326B define two opposing major sides, wherein the sheets 304A, 304B, 326A, and 326B are configured to transmit light through the sheet by internal reflection. (Not shown, see FIG. 1B). The first and second light sources 318A, 318B, 324A, and 324B are positioned to emit light between the two opposing major sides of the first and second sheets 304A, 304B, 326A, and 326B, respectively, suitable for internal reflection and transmission of the light.

As shown, the light therapy system 301 is in the form of a mask shaped to couple with a face of a user. In an embodiment, the first and second sheet 304A, 304B, 326A, and 326B and the first and second light sources 318A, 318B, 324A, and 324B are an example of the light therapy device 200 of FIGS. 2A and 2B. The light therapy system 301 is shown to define a number of apertures 334 shaped and positioned to allow sight through the mask and easy breathing through the nose and mouth of the user. While a system 301 including a first and second sheets 304A, 304B, 326A, and 326B optically coupled to a first and second light sources 318A, 318B, 324A, and 324B, respectively, in the form of a mask defining apertures 334 is illustrated, it will be understood that the system 301 can have other configurations within the scope of the present disclosure. For example, the system 301 can include a single sheet optically coupled to a single light source, such as a single sheet which does not define an aperture. Likewise, in an embodiment, the system 301 includes a single sheet optically coupled to two or more light sources, as discussed further herein with respect to FIGS. 1A-1F.

As above, in an embodiment, each of the first and second sheets 304A, 304B, 326A, and 326B also define micropatterning configured to emit light from within the first and second sheets 304A, 304B, 326A, and 326B onto or towards a portion of skin coupled to the light emission side of the light therapy system 301. In an embodiment, the micropatterning is as illustrated in and described further herein with respect to FIGS. 1B and/or 1D-1F. As shown, the portions of the first and second sheets 304A, 304B, 326A, and 326B defining the micropatterning are positioned distal from the light sources 318A, 318B, 324A, and 324B of the first and second sheets 304A, 304B, 326A, and 326B. In this regard, light emitted from the light therapy system 301 is emitted from a portion of the system 301 that is also distal from the light sources 318A, 318B, 324A, and 324B.

The system 301 is shown to further include a controller 342 operatively coupled to the first light sources 318A and 318B and the second light and a power source 350 operatively coupled to the controller 342 configured to provide power thereto. The controller 342 may be operatively coupled to the first light sources 318A and 318B, second light sources 324A and 324B, and power source 350 in a wired or wireless configuration. In an embodiment, the system 301 includes logic that, when executed by the controller 342, causes the system 301 to perform one or more operations.

In an embodiment, the controller 342 includes logic that, when executed by the controller 342, causes the system 301 to perform operations including emitting first light with the first light sources 318A and 318B into the first sheets 304A and 304B. In an embodiment, the controller 342 includes logic that, when executed by the controller 342, causes the system 301 to perform operations including emitting second light with the second light sources 324A and 324B into the second sheets 326A and 326B.

In the illustrated embodiment, the controller 342 is shown to include first light source illumination logic 346, for controlling emission of first light from the first light sources 318A and 318B, and second light source illumination logic 348, for controlling emission of second light from the second light sources 324A and 324B. In an embodiment, the first light source illumination logic 346 and the second light source illumination logic 348 are configured to modulate a characteristic of the first light and second light, respectively. In an embodiment, such characteristics are selected from the group consisting of a first or second light intensity, a first or second light wavelength range, a first or second light duration, and combinations thereof.

The system 301 is shown to further include a user interface 344 operatively coupled to the controller 342. In an embodiment, the user interface 344 is configured to receive input from a user and emit light from one or more of the first light sources 318A and 318B and second light source 324A and 324B into one or more sheets 304A, 304B, 326A, or 326B of the system 301 based upon the user input. In this regard, a user can tailor or customize light therapy provided by the system 301, such as by selecting a wavelength range, light intensity, therapy duration, and portion of skin 302A or 302B to be treated. Accordingly, in an embodiment, the system 301 includes logic that, when executed by the controller 342, causes the system 301 to perform operations including emitting light, such as light of a particular wavelength range, intensity, duration, and the like, based on a user input. In an embodiment, the user interface 344 is configured to provide or display a list of preprogrammed light therapy regimens from which a user may select and/or modify one or more light therapy regimens.

In an embodiment, the system 301 includes logic that, when executed by the controller 342, causes the system 301 to perform operations including emitting light from one or more light sources 318A, 318B, 324A, and 324B selected by a user, such as with the user interface 344. As discussed further herein, particular light sources may be configured to direct light to a particular portion of micropatterning or emit light of a particular wavelength range configured to be emitted by a particular portion of micropatterning to provide light for receipt by a particular portion of skin 302A or 302B.

Certain embodiments disclosed herein utilize circuitry in order to implement treatment protocols, operably couple two or more components, generate information, determine operation conditions, control an appliance or method, process signals, and/or the like. Circuitry of any type can be used. In an embodiment, circuitry includes, among other things, one or more computing devices such as a processor (e.g., a microprocessor), a central processing unit (CPU), a digital signal processor (DSP), an application-specific integrated circuit (ASIC), a field-programmable gate array (FPGA), or the like, or any combinations thereof, and can include discrete digital or analog circuit elements or electronics, or combinations thereof. In an embodiment, circuitry includes one or more ASICs having a plurality of predefined logic components. In an embodiment, circuitry includes one or more FPGA having a plurality of programmable logic components.

In an embodiment, circuitry includes hardware circuit implementations (e.g., implementations in analog circuitry, implementations in digital circuitry, and the like, and combinations thereof). In an embodiment, circuitry includes combinations of circuits and computer program products having software or firmware instructions stored on one or more computer readable memories that work together to cause a device to perform one or more methodologies or technologies described herein. In an embodiment, circuitry includes circuits, such as, for example, microprocessors or portions of microprocessor, that require software, firmware, and the like for operation. In an embodiment, circuitry includes an implementation comprising one or more processors or portions thereof and accompanying software, firmware, hardware, and the like. In an embodiment, circuitry includes a baseband integrated circuit or applications processor integrated circuit or a similar integrated circuit in a server, a cellular network device, other network device, or other computing device. In an embodiment, circuitry includes one or more remotely located components. In an embodiment, remotely located components are operably coupled via wireless communication. In an embodiment, remotely located components are operably coupled via one or more receivers, transmitters, transceivers, or the like.

In an embodiment, circuitry includes one or more memory devices that, for example, store instructions or data. Non-limiting examples of one or more memory devices include volatile memory (e.g., Random Access Memory (RAM), Dynamic Random Access Memory (DRAM), or the like), non-volatile memory (e.g., Read-Only Memory (ROM), Electrically Erasable Programmable Read-Only Memory (EEPROM), Compact Disc Read-Only Memory (CD-ROM), or the like), persistent memory, or the like. Further non-limiting examples of one or more memory devices include Erasable Programmable Read-Only Memory (EPROM), flash memory, or the like. The one or more memory devices can be coupled to, for example, one or more computing devices by one or more instructions, data, or power buses.

In an embodiment, circuitry of the system 301 includes a computer-readable media drive or memory slot configured to accept signal-bearing medium (e.g., computer-readable memory media, computer-readable recording media, or the like). In an embodiment, a program for causing a system to execute any of the disclosed methods can be stored on, for example, a computer-readable recording medium (CRMM), a signal-bearing medium, or the like. Non-limiting examples of signal-bearing media include a recordable type medium such as any form of flash memory, magnetic tape, floppy disk, a hard disk drive, a Compact Disc (CD), a Digital Video Disk (DVD), Blu-Ray Disc, a digital tape, a computer memory, or the like, as well as transmission type medium such as a digital and/or an analog communication medium (e.g., a fiber optic cable, a waveguide, a wired communications link, a wireless communication link (e.g., transmitter, receiver, transceiver, transmission logic, reception logic, etc.). Further non-limiting examples of signal-bearing media include, but are not limited to, DVD-ROM, DVD-RAM, DVD+RW, DVD-RW, DVD-R, DVD+R, CD-ROM, Super Audio CD, CD-R, CD+R, CD+RW, CD-RW, Video Compact Discs, Super Video Discs, flash memory, magnetic tape, magneto-optic disk, MINIDISC, non-volatile memory card, EEPROM, optical disk, optical storage, RAM, ROM, system memory, web server, or the like.

It should be noted that for purposes of this disclosure, terminology such as "upper," "lower," "vertical," "horizontal," "inwardly," "outwardly," "inner," "outer," "front," "rear," etc., should be construed as descriptive and not limiting the scope of the claimed subject matter. Further, the use of "including," "comprising," or "having" and variations thereof herein is meant to encompass the items listed thereafter and equivalents thereof as well as additional items. Unless limited otherwise, the terms "connected," "coupled," and "mounted" and variations thereof herein are used broadly and encompass direct and indirect connections, couplings, and mountings. The term "about" means plus or minus 5% of the stated value.

The principles, representative embodiments, and modes of operation of the present disclosure have been described in the foregoing description. However, aspects of the present disclosure which are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure, as claimed.

While illustrative embodiments have been illustrated and described, it will be appreciated that various changes can be made therein without departing from the spirit and scope of the invention.

The invention claimed is:

1. A light therapy device configured to apply light to a portion of skin, the light therapy device comprising:
   a first sheet defining two opposing major sides, wherein the first sheet is configured to transmit light through the first sheet by internal reflection, and wherein a portion of a light emission side of the two opposing major sides is configured to couple with the portion of skin and defines first micropatterning configured to emit light from within the first sheet;
   a first light source configured to emit first light having a first wavelength range into the first sheet between the two opposing major sides;
   a second sheet defining two second opposing major sides, wherein the second sheet is configured to transmit light by internal reflection, and wherein a portion of a second light emission side of the two second opposing major sides defines second micropatterning configured to emit light;

a second light source configured to emit second light in a second wavelength range different than the first wavelength range into the second sheet between the two second opposing major sides; and an aperture defined by the first sheet and the second sheet, the aperture being shaped to accommodate an eye, wherein the first and second sheets are optically isolated from one another, wherein the first micropatterning is configured to emit the first light at a first intensity and to emit the second light at a second intensity different than the first intensity; and wherein the second micropatterning is configured to emit the second light at a third intensity different than the first intensity.

2. The light therapy device of claim 1, wherein the first micropatterning is positioned distal from the first light source.

3. The light therapy device of claim 1, wherein the first sheet defines third micropatterning disposed on a second portion of the light emission side.

4. The light therapy device of claim 1, further comprising a filter configured to filter light of a wavelength range emitted from the first micropatterning.

5. The light therapy device of claim 1, further comprising a mirror positioned to reflect light within the first sheet.

6. The light therapy device of claim 1, wherein the light emission side of the first sheet is configured to face the portion of skin when the first sheet is coupled to the portion of skin, and wherein the first sheet is configured to conform to the portion of skin.

7. A system for light therapy configured to apply light to a portion of skin, the system comprising:

a first sheet defining two opposing major sides, wherein the first sheet is configured to transmit light through the first sheet by internal reflection, and wherein a portion of a light emission side of the two opposing major sides is configured to couple with the portion of skin and defines first micropatterning configured to emit light from within the first sheet;

a first light source configured to emit first light having a first wavelength range into the first sheet between the two opposing major sides;

a second sheet defining two second opposing major sides, wherein the second sheet is configured to transmit light by internal reflection, and wherein a portion of a second light emission side of the two second opposing major sides defines second micropatterning configured to emit light;

a second light source configured to emit second light in a second wavelength range different than the first wavelength range into the second sheet between the two second opposing major sides; and an aperture defined by the first sheet and the second sheet, the aperture being shaped to accommodate an eye, wherein the first and second sheets are optically isolated from one another;

wherein the first micropatterning is configured to emit the first light at a first intensity and to emit the second light at a second intensity different than the first intensity; and wherein the second micropatterning is configured to emit the second light at a third intensity different than the first intensity; and a controller operatively coupled to the first light source and the second light source, the controller including logic that, when executed by the controller, causes the system to perform operations including:

emitting first light with the first light source into the first sheet; and emitting second light with the second light source into the second sheet.

* * * * *